United States Patent [19]

Aubard et al.

[11] Patent Number: 4,734,428

[45] Date of Patent: Mar. 29, 1988

[54] AMINOETHYLIMIDAZOLE AND CYTOPROTECTIVE AND GASTRIC ANTISECRETORY COMPOSITION CONTAINING THE SAME

[75] Inventors: Gilbert G. Aubard, Palaiseau; Jacques Bure, Neuilly sur Seine; Agnès G. Grouhel, Meudon; Jean-Louis Junien, Paris; Véronique J. Lelievre, Paris; Xavier B. Pascaud, Paris; Claude P. Roux, Paris, all of France

[73] Assignee: Jouveinal S.A., Paris, France

[21] Appl. No.: 872,481

[22] Filed: Jun. 10, 1986

Related U.S. Application Data

[63] Continuation of Ser. No. 683,474, Dec. 19, 1984, abandoned.

[30] Foreign Application Priority Data

Jan. 11, 1984 [FR] France ................................ 84 00351

[51] Int. Cl.$^4$ .................. A61K 31/415; C07D 233/61
[52] U.S. Cl. ..................................... 514/399; 548/341
[58] Field of Search .......................... 548/341; 514/399

[56] References Cited

U.S. PATENT DOCUMENTS 3,912,689 10/1975 Bechara et al. ...................... 548/341
4,320,134 3/1982 Iizuka et al. ......................... 514/399
4,579,862 4/1986 Manley et al. ....................... 548/341

OTHER PUBLICATIONS

Chem. Abst. 102, 62244r (1985).

Primary Examiner—Henry R. Jiles
Assistant Examiner—Kurt G. Briscoe
Attorney, Agent, or Firm—Cushman, Darby & Cushman

[57] ABSTRACT

Aminoethyl imidazole of formula:

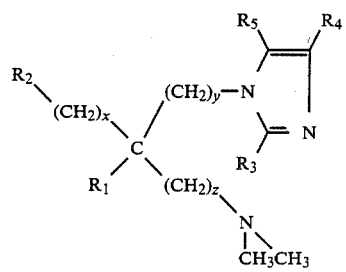

in which $R_1$ is a lower alkyl, $R_2$ is a phenyl or phenoxy radical, optionally substituted by a halogen atom or a lower alkoxy radical, $R_3$, $R_4$ and $R_5$ are a hydrogen atom or a lower alkyl radical and x, y and z have the value 0 or 1, but the values of y and z cannot be the same, together with their acid addition salts with acids.

Cytoprotective medicament.

5 Claims, No Drawings

AMINOETHYLIMIDAZOLE AND CYTOPROTECTIVE AND GASTRIC ANTISECRETORY COMPOSITION CONTAINING THE SAME

This is a continuation of application Ser. No. 683,474, filed Dec. 19, 1984, now abandoned.

The present invention relates to novel imidazole derivatives substituted in their 1-position by a 2-N,N-dimethylaminoethyl radical, their preparation process and their use in human and veterinary medicine.

The products according to the invention are in accordance with the following general formula:

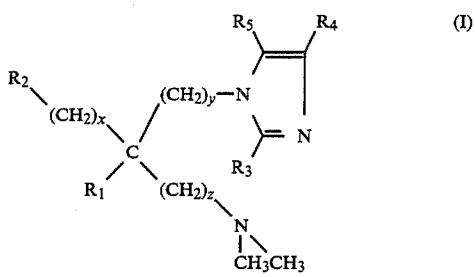

in which $R_1$ stands for lower alkyl, $R_2$ is either lower alkyl, or a phenyl or phenoxy radical optionally substituted by a halogen atom, a lower alkoxy radical or a phenyl radical, $R_3$, $R_4$ and $R_5$ can be the same or different and are hydrogen atoms, lower alkyl radicals or phenyl radicals, x, y and z have a value of 0 or 1, but the values of y and z must not be the same.

In general terms, so-called lower radicals have 1 to 6 carbon atoms in a straight or branched chain. When $R_2$ is a phenoxy or phenyl radical, it can be multisubstituted or monosubstituted. When it is monosubstituted, the monosubstitution is preferably in the para-position by a halogen atom, such as a chlorine atom, or by a lower alkoxy radical, such as a methoxy radical, or by an aromatic radical, such as the phenyl radical.

The invention also covers the mono- or di-addition salts of these derivatives, particularly mineral acids, such as halohydrates, sulphates, phosphates or those of organic acids such as maleates, citrates, malates, tartrates, methane sulphonates, camphosulphonates, benzoates, etc.

Obviously, the invention applies both to the racemic forms of these products and to their optically active forms, which can be obtained by known means, such as e.g. the resolution of the racemic forms by means of optically active acids, or by preparation from optically active structures.

Pharmacological studies have shown that, apart from a low toxicity, the products according to the invention also have a particularly remarkable cytoprotective activity suitable for the preventative or curative treatment of ailments to the gastrointestinal tract. Thus, the invention is also directed at a pharmaceutical composition containing a compound of formula (I) or a salt thereof, combined with a pharmacologically acceptable vehicle. The compound generally represents 10 to 50 parts by weight of the composition, whilst the vehicle represents 90 to 40 parts by weight thereof.

The products according to the invention are prepared by N-alkylation in the 1-position of the appropriate imidazole radical by means of 2-N,N-dimethylaminoethyl halides in accordance with the following reaction:

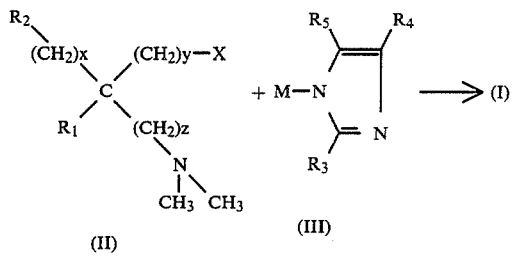

In reagents (II) and (III), $R_1$, $R_2$, $R_3$, $R_4$ and $R_5$, x, y and z have the meanings given hereinbefore, X is a halogen atom, such as a chlorine atom and M is a hydrogen atom or a metal atom, such as silver, sodium or potassium. The halides (II) can be obtained from the corresponding amino alcohols, e.g. by reacting thionyl chloride, in the manner described in "Organic Syntheses", Coll., Vol. IV, p.333 or other appropriate methods described in the literature. The starting amino alcohols are prepared by known methods, such as those described in French Pat. Nos. 912,577 and 7,108,700.

Some of the imidazole (III) compounds are commercially available, or are prepared by known methods consisting of reacting with the suitable imidazole metals or their hydroxyls, hydrides, alkoxides or amides. Derivatives (III) obtained can either be separated, or prepared in situ in a preliminary manner in the reaction medium for preparing the products according to the invention.

The condensation reaction for the preparation of the products according to the invention can be carried out in different media:

in a monophase medium: in anhydrous and inert solvents representing 3 to 100 times and preferably 8 to 15 times the weight of the two reagents and constituted by halogenated hydrocarbons, such as carbon tetrachloride, dichloromethane and chloroform, aromatic hydrocarbons, such as benzene and toluene, ethers, such as diethyl ether, cyclic ethers, such as tetrahydrofuran and dioxan, optionally alkoxylated saturated aliphatic hydrocarbons, such as dimethoxyethane, hexane and heptane, ketones, such as acetone, methyl ethyl ketone, sulphoxides, such as dimethyl sulphoxide, amides, such as dimethyl formamide, dimethyl acetamide, hexamethylphosphorotriamide, etc;

in a two-phase medium in the presence of water and an aromatic solvent, such as benzene or toluene. The reaction then takes place in a very alkaline medium in the presence of sodium or potassium hydroxide and in the presence of a so-called phase transfer catalyst, such as quaternary ammonium salts, which can be tetramethylammonium, triethylbenzylammonium or trimethyloctadecylammonium, bromides, chlorides, iodides, hydrogensulphates or tetrafluoroborates, or phosphonium derivatives, such as tributylhexadecyl bromide. There are 10 to 30 parts by volume of water for 100 parts by volume of the organic phase. Water and organic solvent together represent 3 to 100 times and preferably 8 to 15 times the weight of the two reagents. The catalyst represents 0.5 to 5 parts of the weight of the two reagents.

Usually, 0.5 to 2 moles of derivative (III) are used per mole of derivative (II) and preferably there is an equimolar ratio between these two reagents.

The reactions take place at temperatures between 20° and 150° C., as a function of the type of reaction and the solvents used. However, preference is given to the use of the condensation reaction in accordance with the so-called phase transfer method at a temperature between 50° and 100° C. The reactions last between 1 and 10 hours and preferably between 2 and 5 hours.

The products according to the invention are separated from the reaction medium by known processes, such as extraction, distillation, crystallization and separative chromatography. Their identity and purity are checked by conventional methods, such as spectrographic methods (UV, IR, NMR, mass), chromatographic methods (TLC, LHPC) or physicochemical methods (melting point m.p., refractive index $n_D^{20}$).

The following examples serve to illustrate the products according to the invention in a nonlimitative manner.

EXAMPLE 1

1A:
1-[(2-phenyl-2-ethyl)-2-N,N-dimethylaminoethyl]-imidazole $R_1$=ethyl, $R_2$=phenyl, $R_3$=$R_4$=$R_5$=hydrogen x=z=0, y=1.

1B:
1-[(1-phenyl-1-ethyl)-2-N,N-dimethylaminoethyl]-imidazole $R_1$=ethyl, $R_2$=phenyl, $R_3$=$R_4$=$R_5$=hydrogen x=y=0, z=1.

100 ml of anhydrous dimethylformamide (DMF) and 7.1 g of 80% (wt/wt) sodium hydride (5.66 g—0.236 mole) are introduced into a 1 liter reactor under a nitrogen atmosphere.

A solution of 16.0 g (0.236 mole) of imidazole in 100 ml of DMF are added, accompanied by stirring, to the greyish suspension over a period of approximately 15 minutes and at a temperature below 25° C. A greenish solution is obtained, which is stirred for 20 minutes at ambient temperature.

Over a period of 20 minutes and at a temperature of 20° C. are then introduced 50.0 g (0.236 mole) of 2-phenyl-2-ethyl-2-N,N-dimethylaminoethyl chloride dissolved in 100 ml of DMF.

The mixture is stirred for 2½ hours at ambient temperature, then precipitated in 1000 ml of ice water and extracted with ether. The combined ethereal phases are washed with water up to neutrality and then dried over sodium sulphate.

The ether is eliminated by vacuum distillation on the water bath. 46 g of oily residue are obtained, which is treated to obtain products 1A and 1B.

1A:
The residue is taken up in 400 ml of boiling cyclohexane. When left at ambient temperature, the solution crystallizes. The crystals are filtered and dried at 60° C. in vacuo: weight 19.0 g, yield 33.1%, m.p. 91° C.

1A, Hemimaleate 13.25 g (0.054 mole) of the above product are salified with 6.6 g (0.057 mole) of maleic acid in 130.0 ml of ethanol under reflux, giving 17.6 g of white crystals, yield 90.7%, m.p. 124° C.

1A, Methiodide 14.0 g (0.0575 mole) of product are dissolved in 85.0 ml of anhydrous acetone, followed by the rapid addition of 24.5 g (0.173 mole) of methyl iodide and stirring takes place overnight at ambient temperature. 20.2 g of pale yellow crystals are obtained, yield 91.2%, m.p. 163° C.

1B:
The cyclohexane for crystallizing the base of product 1A is eliminated by vacuum distillation. The residue obtained (28.0 g) is purified by silica column chromatography. Elution by a cyclohexane:ethylacetate:methanol mixture 12:3:1 (v/v/v) makes it possible to collect a pure fraction by thin layer chromatography. Weight 8.7 g, yield 15.2%, $n_D^{20}$=1.5471.

The magnetic resonance spectrography of the proton and the mass spectrography of the products concur and confirm that the products 1A and 1B have the indicated structures.

EXAMPLE 2

2A:
1-[(2-phenyl-2-ethyl)-2-N,N-dimethylaminoethyl]-2-methylimidazole $R_1$: ethyl, $R_2$=phenyl, $R_3$=methyl, $R_4$=$R_5$=hydrogen x,z=0, y=1.

2B:
1-[(1-phenyl-1-ethyl)-2-N,N-dimethylaminoethyl]-2-methylimidazole $R_1$=ethyl, $R_2$=phenyl, $R_3$=methyl, $R_4$=$R_5$=hydrogen x=y=0, z=1.

300.0 ml of toluene, 11.6 g (0.142 mole) of 2-methylimidazole, 30.0 g (0.142 mole) of 2-phenyl-2-ethyl-2-N,N-dimethylaminoethyl chloride, followed by 45.0 ml of aqueous sodium hydroxide solution (d=1.33) and 2.7 g of hexadecyltributylphosphonium bromide are introduced into a 1 liter reactor.

Accompanied by vigorous stirring, the mixture is heated to 80° to 85° C. for 2 hours. After cooling the aqueous phase is eliminated and the toluene phase washed by extraction with a saturated sodium chloride solution.

The toluene phase is dried over sodium sulphate and then the toluene is eliminated by distillation in vacuo and on the water bath.

The oily residue (38.5 g) is treated in the same way as in example 1 for separating products 2A and 2B. Following treatment and purification, the following are obtained:

2A, Hemimaleate:
Weight 17.0 g, yield 24.5%, m.p. 111.5° C.
2B: Weight 7.0 g, yield 19.2%, m.p. 67.5° C.

The spectrographic methods used unambiguously confirm the structures of products 2A and 2B.

The products of examples 3 to 8 are described in the following table 1. They are prepared in accordance with the operating procedure of example 2 from products according to the general formulas II and III, in which the meanings of $R_1$, $R_2$, $R_3$, $R_4$, $R_5$, x, y and z are defined. For the products of formula II, X is a chlorine atom, whilst for the products of formula III, M is a sodium or hydrogen atom.

TABLE 1

| EX. No. | $R_1$ | $R_2$ | $R_3$ | $R_4$ | $R_5$ | x | A y = 1 z = 0 | B y = 0 z = 1 |
|---|---|---|---|---|---|---|---|---|
| 3 | $C_2H_5$ |  | H |  | 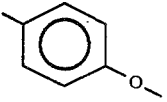 | | 0 | Base - m.p. = 183° C. Yield = 19.3% Hemimaleate mp = 142° C. | base m.p. = 133° C. Yield = 31.4% |
| 4 | $C_2H_5$ |  | $C_2H_5$ | $CH_3$ | H | 0 | Base - m.p. = 56° C. Yield = 12.2% | Base - Oil Yield = 14.75% |
| 5 | $C_2H_5$ |  |  | H | H | 0 | Base - Oil Yield = 7% Hemimaleate m.p. = 135° C. | Base m.p. = 80.5° C. Yield = 14.2% |
| 6 | $CH_3$ | $CH_3$ | H | H | H | 0 | Base - Oil $n_D^{20}$ = 1.501 Yield = 19% | Base - Oil $n_D^{20}$ = 1.469 Yield = 15% |
| 7 | $C_2H_5$ |  | H | H | H | 1 | Base - Oil Yield = 27.9% Dicamphosulphonate m.p. = 128° C. | Base m.p. = 60° C. Yield = 3.7% |
| 8 | $C_5H_{11}$ |  | H | H | H | 0 | Base - Oil $n_D^{20}$ = 1.542 Yield = 27.5% | Base - Oil $n_D^{20}$ = 1.532 Yield = 17.6% |

TABLE 2

| EX. NO. | $R_1$ | $R_2$ | X | PRODUCT |
|---|---|---|---|---|
| 10 | $CH_3$ | 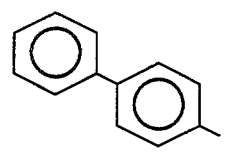 | 1 | Base $n_D^{20}$ = 1.5540 Yield = 34% |
| 11 | $CH_3$ | 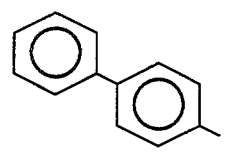 | 0 | Base m.p. = 125.1° C. Yield = 15% |

EXAMPLE 9

1-[(2-p-methoxybenzyl-2-methyl)-2-N,N-dimethylaminoethyl]imidazole dihemimaleate $R_1$=methyl, $R_2$=p-methoxybenzyl, $R_3$=$R_4$=$R_5$=hydrogen, x=1, z=0, Y=1.

200 ml of toluene, 5.5 g (0.081 mole) of imidazole, 19.6 g (0.081 mole) of 2-(p-methoxybenzyl)-2-methyl-2-N,N-dimethylaminoethyl chloride, 32.6 ml of aqueous sodium hydroxide solution (d=1.33) and 2.0 g of hexadecyl tributylphosphonium bromide are introduced into a 500 ml reactor.

The mixture is heated for 4 hours to 85° to 90° C., accompanied by vigorous stirring and then, after cooling, the aqueous phase is removed.

The toluene phase is washed with a saturated, dehydrated sodium chloride solution and then the toluene is removed by distillation. A residue of 22.0 g is obtained, which is purified by silica column chromatography.

Elution by a cyclohexane:ethylacetate:methanol mixture 100:40:15 (v/v/v) makes it possible to separate the desired product. Weight 9.8 g, yield 46.1%.

8.4 g (0.032 mole) of product are salified by 7.75 g (0.067 mole) of maleic acid in 150 ml of ethanol under reflux. After cooling, the crystals obtained are filtered. Weight 10.0 g, yield 61.8%, m.p. 122.5° C.

On the basis of suitable reagents and the operating procedure described for example 9, the products of examples 10 and 11 are obtained (table 2) in which $R_3$=$R_4$=$R_5$=H, z=0 and y=1.

EXAMPLE 12

1-[(2-phenyl-2-ethyl)-2-N,N-dimethylaminoethyl]-imidazole.

The chlorinated derivative corresponding to the levorotatory isomer 2-phenyl-2-ethyl-N,N-dimethylaminoethanol is prepared in the usual way. The product obtained is condensed with imidazole according to the procedure described in example 2. After treatment and purification, 18.8 g of oily products are obtained. Yield 38.6%, $[\alpha]_D^{20}$= −27.8° (EtOH c=1%)

Hemimaleate 18 g of the above product (0.074 mole) are salified under ethanol reflux by 9 g (0.078 mole) of maleic acid, giving 20 g of white crystals. Yield 75%, m.p. 125° C., $[\alpha]_D^{20}$= −29.2° ($H_2O$ c=2%).

The toxicological and pharmacological tests described in the following part demonstrate that the products according to the invention are only slightly toxic and have interesting cytoprotective activities.

The acute toxicity of the products was investigated in male SWISS/IOPS mice weighing approximately 22 g. The 50% lethal dose ($LD_{50}$) was calculated by the method of L. J. REED and H. MUNCH (Am. J. Hyg. 1939-37-493) 14 days following the oral intraperitoneal treatment of batches of 10 animals per dose and on the basis of 4 to 6 doses per product. The results of this investigation are given in table 3 for the products of examples 1 to 8 and in table 4 for the products of examples 9 to 12.

TABLE 3

ACUTE TOXICITY - Ex. 1 to 8

| PRODUCT CODE | $LD_{50}$ % mg/kg$^{-1}$ Oral route | i.p. route | PRODUCT CODE | $LD_{50}$ % mg/kg$^{-1}$ Oral route | i.p. route |
|---|---|---|---|---|---|
| Ex. 1A, H. maleate JO 1193 | 559 | 326 | Ex. 1B JO 1194 | 285 | 145 |
| Ex. 2A, H. maleate JO 1230 | 500 | 157 | Ex. 2B JO 1231 | 393 | 137 |
| Ex. 3A, H. maleate JO 1323 | >1150 | | Ex. 3B JO 1324 | >1152 | |
| | | | Ex. 4B JO 1325 | 298 | 47 |
| | | | Ex. 5B JO 1334 | 840 | |
| Ex. 6A JO 1331 | >1180 | | Ex. 6B JO 1332 | >1180 | |
| Ex. 7A, Di Camphos. JO 1365 | 480 | | Ex. 7B JO 1364 | 384 | |
| Ex. 8A JO 1368 | 287 | | Ex. 8B JO 1367 | 562 | 346 |

TABLE 4

ACUTE TOXICITY - Ex. 9 to 12

| PRODUCT CODE | $LD_{50}$ % mg/kg$^{-1}$ Oral route | i.p. route |
|---|---|---|
| EX. 9, Di H. maleate JO 1250 | 758 | 231 |
| EX. 10 JO 1233 | 86 | 32 |
| EX. 11 JO 1366 | 183 | |
| EX. 12, H. maleate JO 1274 | 780 | |

The cytoprotective activity was investigated in connection with the stressing of the gastric mucosa caused by ethanol.

The cytoprotection test was carried out in accordance with the procedure described by A. ROBERT et al (Gastroenterology 1979-77-433). Batches of six male Sprague Dawley rats, which had not received solid food for 24 hours before the test, received by the oral route 1 ml/rat of absolute ethanol, after receiving the product to be tested 30 minutes beforehand by the subcutaneous routine for 1 hour beforehand by the oral route. One hour after ingesting the ethanol, the rats were killed by stretching and their stomachs were carefully removed, opened along the greater curvature, washed under running water and spread out. The ulcerations were then marked and measured under a binocular lamp. An index representing the sum of the lengths of the ulcers is then determined for each rat and the mean value of these indexes for each batch is calculated and compared with that of the control batch using the Student "t" test. The 50% effective dose ($ED_{50}$) is then graphically determined when possible. In other cases, the percentage inhibition obtained with the aid of the maximum tested dose is given. The results are given in table 5 for the products of examples 1 to 8 and in table 6 for the products of examples 9 to 12.

TABLE 5

CYTOPROTECTIVE ACTIVITY- Ex. 1 to 8

| PRODUCT CODE | $LD_{50}$ % mg/kg$^{-1}$ Oral route | s.c. route | PRODUCT CODE | $LD_{50}$ % mg/kg$^{-1}$ Oral route | s.c. route |
|---|---|---|---|---|---|
| Ex. 1A, H. maleate JO 1193 | $ED_{50\%}$ 13.0 | $ED_{50\%}$ 11.0 | Ex. 1B JO 1194 | $ED_{50\%}$ 7.1 | $ED_{50\%}$ 8.1 |
| Ex. 2A, H. maleate JO 1230 | $ED_{50\%}$ 12.0 | $ED_{50\%}$ 12.6 | Ex. 2B JO 1231 | $ED_{50\%}$ 12.0 | $ED_{50\%}$ 10.0 |
| | | | Ex. 3B JO 1324 | $ED_{50\%}$ 26.0 | |
| | | | Ex. 4B JO 1325 | | $ED_{50\%}$ 4.0 |
| Ex. 7A, Di Camphos. JO 1365 | | $ED_{50\%}$ 26.6 | Ex. 7B JO 1364 | | $ED_{50\%}$ 8.5 |
| Ex. 8A JO 1368 | | $ED_{50\%}$ 25.0 | Ex. 8B JO 1367 | | $ED_{50\%}$ 9.0 |

TABLE 6

CYTOPROTECTIVE ACTIVITY - Ex. 9 to 13

| PRODUCT CODE | LD × % mg/kg$^{-1}$ s.c. route |
|---|---|
| EX. 10 JO 1233 | $ED_{50\%}$ 10.0 |
| EX. 11 JO 1366 | $ED_{40\%}$ 10.0 |
| EX. 12, H. maleate JO 1274 | $ED_{50\%}$ 5.3 |

The results summarized in the preceding tables show that the products according to the invention provide a significant protection against hemorrhages and ulcerations of the gastric mucosa caused in the rat by the absorption of absolute ethanol. This activity appears both when using the parenteral and the oral route. The $ED_{50}$ values relative to these two routes are roughly equivalent for the compounds tested by the two routes (JO 1193, 1194, 1230 and 1231).

It is of particular interest to note that this activity occurs at doses far removed from the toxic doses (1/20 or 1/40 of the $LD_{50}$).

The products according to the invention are also able to inhibit thromboxane synthetase and this activity can be linked with the previously described cytoprotective properties.

Thus, on very briefly summarizing recent works, it would appear that the prostanoids play a determinant part in the vasoactive phenomena of inflammation. Thus, in certain cases of ulcerous information, a reduction of $PGE_2$ and $PGI_2$ synthesis has been gastrically and duodenally demonstrated, these products being mediators having acid antisecretory effects, as well as stimulating alkaline secretion and acting as cytoprotectors.

Conversely, the effects of $TXA_2$ are the opposite of those of $PGI_2$. Thus, the relationship between these two prostanoid types is very important and becomes more advantageous with an increase of PG and a decrease of TX. The inhibition of thromboxane synthetase by products according to the invention is consequently significant and/or complementary of the cytoprotective activity.

The test performed was carried out in vitro on washed rabbit platelets. It was based on the publications of NEEDLEMAN (1977. Proc. Natl. Acad. Sci. 74, 1716) and SALMON (1982, Cardiovascular Pharmacol. of the Prostaglandins—Raven Press N.Y. pp. 7 to 22). It makes it possible both to determine the reduction of the synthesis of $TXB_2$ and also the possible increase of the synthesis of $PGE_2$. Thus, it is possible to determine the activity of the products on the PG:TX ratio.

The results given in the following tables are expressed in CEx%, i.e. in micromolar concentrations per liter permitting an inhibition by x% of the synthesis of $TXB_2$. In the adjacent column, the symbol + means that the effect also causes an increase in the synthesis of $PGE_2$.

In this test, 1-benzyl imidazole recognised as a thromboxane synthetase inhibitor on human platelets (HSIN-HSIUNG TAI—BARBARA YUAN—Bioch, Biophys. Res. Comm. 1978 1 80 p. 237) was used as the reference substance. Certain products according to the invention have an equal to clearly superior activity to this product and in particular to the product designated JO 1193, 1368, 1367 and 1250.

TABLE 8

RESULTS OF EXAMPLES 9 to 12

| PRODUCT CODE | Inh. TX $B_2$ | Incr. $PGE_2$ |
|---|---|---|
| EX. 9, | $CE_{50\%} = 4.5$ | + |
| EX. 10 JO 1233 | $CE_{50\%} = 13.2$ | + |
| EX. 11 JO 1366 | $CE_{50\%} = 11.2$ | + |
| EX. 12, H. maleate JO 1274 | $CE_{50\%} = 11.3$ | + |
| Ref. 1-Benzyl-Imidazole | $CE_{50\%} = 13.4$ | |

The products according to the invention are administered to humans by the routes which are suitable for the nature and gravity of the ailment to be treated and in therapeutic forms which are compatible with the envisaged administration route. These different forms prepared on the basis of the products according to the invention in the form of the base or their different salts are prepared by per se known methods.

The different preparations can also contain the products according to the invention combined with compatible active principles, such as bacteriostatic, antibiotic, antispasmodic, anesthetic, analgesic, antiinflammatory and similar agents. Examples of these preparations are tablets, dragees, capsules, powder, solutions, suspensions, gels and suppositories. As a non-limitative illustration of their production, reference is made hereinafter to the production of tablets and injectable isotonic solutions using the active principles according to the invention.

| (1) Tablets | mg |
|---|---|
| Active substance according to example 2A | 50.0 |
| Lactose | 26.5 |
| Mannitol | 55.0 |
| Officinal white sugar | 11.0 |
| Polyethylene glycol 6000 | 5.0 |
| Magnesium stearate | 2.0 |
| Gelatin | 0.5 |
| Wheat starch | 50.0 |
| TOTAL | 200.0 |

The gelatin and officinal white sugar are separately dissolved in water. The two solutions are mixed and polyethylene glycol 6000 is added thereto. Moreover, the lactose and mannitol are intimately mixed, followed by the addition in succession of the active substance of example 2A, the wheat starch and then the previously obtained solution. The paste is dried, granulated and screened, whilst adding the magnesium stearate and wheat starch thereto. The product obtained is homogenized and compressed at a rate of 200.0 mg per tablet.

TABLE 7

RESULS OF EXAMPLES 1 to 8

| PRODUCT CODE | Inh. Tx $B_2$ | Incr. $PGE_2$ | PRODUCT CODE | Inh. TX $B_2$ | Incr. $PGE_2$ |
|---|---|---|---|---|---|
| Ex. 1A, H. maleate JO 1193 | $CE_{50\%} = 3.7$ | + | Ex. 1B JO 1194 | $CE_{50\%} = 17.4$ | + |
| Ex. 2A, H. maleate JO 1230 | $CE_{10\%} = 50$ | | Ex. 2B JO 1231 | $CE_{18\%} = 50$ | |
| Ex. 5A JO 1333 | $CE_{50\%} = 50$ | | Ex. 5B JO 1334 | $CE_{20\%} = 50$ | |
| Ex. 6A JO 1331 | $CE_{41\%} = 50$ | | Ex. 6B JO 1332 | $CE_{50\%} = 50$ | |
| Ex. 7A, Di Camphos. JO 1365 | $CE_{50\%} < 1$ | + | Ex. 7B JO 1364 | $CE_{35\%} = 100$ | |
| Ex. 8A JO 1368 | $CE_{50\%} = 0.56$ | + | Ex. 8B JO 1367 | $CE_{50\%} = 2.15$ | + |

| (2) Injectable isotonic solution | mg |
|---|---|
| Active substance according to example 1A | 10 |
| Sodium chloride | 9 |
| Distilled water (quantity sufficient for) | 1 ml |

The isotonic solution is portioned out into ampoules of appropriate volume which, after sealing, are sterilized by per se known thermal means, or the solution is sterilized by filtration, portioned out into ampoules, followed by the sealing thereof, all these operations being carried out in a sterile atmosphere. In the latter case, it is preferable to add to the formula described, 1% of benzyl alcohol as the bacteriostatic agent, i.e. 10 mg of this alcohol per ml of solution.

We claim:

1. Aminoethyl imidazole of formula:

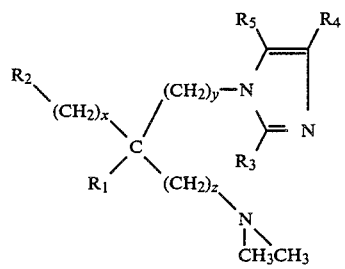

wherein
$R_1$ is lower alkyl,
$R_2$ is lower alkyl, phenyl or phenoxy, optionally substituted by halogen, lower alkoxy or phenyl,
$R_3$, $R_4$ and $R_5$, each represent hydrogen,
x, y and z are 0 or 1 with the proviso that y and z cannot be the same, or a pharmaceutically acceptable addition salt with an acid.

2. The aminoethyl imidazole of claim 1, wherein $R_2$ is monosubstituted in the para-position.

3. The aminoethyl imidazole of claim 1 which is 1-[(2-phenyl-2-ethyl)-2-N,N-dimethylaminoethyl]-imidazole or a salt thereof.

4. The aminoethyl imidazole of claim 1 which is 1-[(1-phenyl-1-ethyl)-2-N,N-dimethylaminoethyl]-imidazole or a salt thereof.

5. A pharmaceutical composition having a cytoprotective and gastric antisecretory activity, said composition comprises a pharmaceutically acceptable carrier and a therapeutically effective amount of an aminoethyl imidazole of formula:

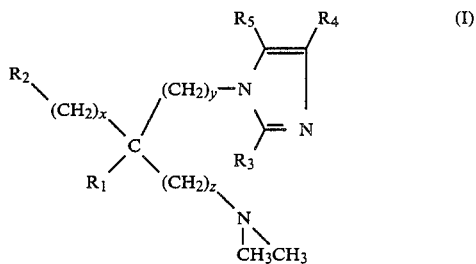

wherein
$R_1$ is lower alkyl,
$R_2$ is lower alkyl, phenyl or phenoxy, optionally substituted by halogen, lower alkoxy or phenyl,
$R_3$, $R_4$ and $R_5$, each represent hydrogen,
x, y and z are 0 or 1 with the proviso that y and z cannot be the same,
or a pharmaceutically acceptable salt with an acid.

* * * * *